United States Patent [19] [11] 3,998,641
Schranz et al. [45] Dec. 21, 1976

[54] PHOTOGRAPHIC MATERIAL CONTAINING YELLOW COUPLERS

[75] Inventors: Karl-Wilhelm Schranz, Odenthal-Hahnenberg; Friedrich-Wilhelm Kunitz, Leverkusen, both of Germany

[73] Assignee: Agfa-Gevaert Aktiengesellschaft, Leverkusen, Germany

[22] Filed: Dec. 3, 1974

[21] Appl. No.: 529,038

[30] Foreign Application Priority Data

Dec. 10, 1973 Germany .......................... 2361471

[52] U.S. Cl. .................................. 96/100; 96/56.3
[51] Int. Cl.² ........................................ G03C 1/40
[58] Field of Search ............................ 96/100, 56.3

[56] References Cited

UNITED STATES PATENTS

| | | | |
|---|---|---|---|
| 2,319,426 | 5/1943 | Middleton et al. | 96/56.3 |
| 3,689,271 | 9/1972 | Nittel et al. | 96/100 |
| 3,841,880 | 10/1974 | Kertel | 96/100 |
| 3,843,366 | 10/1974 | Van Poucke et al. | 96/100 |

*Primary Examiner*—J. Travis Brown
*Attorney, Agent, or Firm*—Connolly and Hutz

[57] ABSTRACT

Diffusion-fast yellow couplers for color photographic silver halide materials with at least one silver halide emulsion layer are provided containing a substituted or unsubstituted 2-cyclotetramethylene sulfone group in a non-coupling position of the coupler molecule which couplers are excellently emulsifiably in color photographic emulsions, are highly reactive and stable under heat and tropic conditions. The dyes produced from them by chromogenic development in color developers containing aromatic components of the p-phenylene diamine series which contains at least one primary amino group are eminently stable under heat and tropic conditions, have a low side absorptions in the unwanted region of the spectrum and low fog values.

5 Claims, No Drawings

PHOTOGRAPHIC MATERIAL CONTAINING YELLOW COUPLERS

The invention to a color photographic material which has at least one silver halide emulsion layer and contains a diffusion-fast yellow coupler.

By photographic yellow couplers are meant compounds which react with oxidation products of photographic color developers, in particular those of the phenylene diamine series, to form yellow dyes. Photographic color couplers must satisfy numerous requirements. For example they should react as rapidly as possible with the oxidized color developer to form a dye. The dye formed by chromogenic development should as far as possible absorb only in the desired spectral range as side absorptions in other regions of the spectrum are disadvantageous. The dyes produced should as far as possible be lightfast and should be stable even under extreme conditions such as the high temperature and humidity which occur in the tropics. Sufficient stability to tropical conditions is of course also required of the color couplers incorporated in the light-sensitive material because otherwise the unprocessed material or the image produced from it would tend to undergo yellowing. The couplers must also be sufficiently stable against gaseous reducing or oxidizing agents and must be fixed in a diffusion-fast form in the image layer and should be produced as a very fine grain by chromogenic development.

One problem which has not yet been solved satisfactorily in practice is that of permanently incorporating the couplers in a finely divided form in the hydrophilic colloid layers of photographic materials so that they do not diffuse out of the layers or in some other way deleteriously affect the photographic or mechanical properties of the layers. Hydrophobic couplers must be added to the emulsions in the form of stable dispersions. It is frequently observed that if photographic materials containing hydrophobic couplers are stored for some time, the layers become cloudy, which is due to crystallization of the coupler. It is occasionally possible to reduce the tendency for color couplers to crystallize by introducing certain organic groups into the coupler molecule, e.g. suitably substituted phenoxy groups. Examples of this are given in U.S. Pat. Nos. 2,423,730; 2,474,293 and 2,908,573. The first two of these patent specifications describe exclusively cyan couplers and the last describes all commonly used color couplers which contain such substituted phenoxy groups.

The demand for couplers which can be easily emulsified has in the past lead to attempts to produce couplers having a low melting point as possible, because it is known that such couplers generally have less tendency to crystallize from the photographic layers than a coupler having a high melting point. Couplers having low melting points, however, are known to be often difficult to purify. Reference is made in this connection to the same problems involved and disclosed in British application Ser. No. 01077/74. Although the compounds described in the said British patent application can be prepared quite easily and are very readily emulsifiable, it can be expected that even minute traces of thiophenol still adhering to the color coupler incorporated in a photographic silver halide emulsion layer would have a powerful inhibiting effect on development. Moreover, it can be expected that the reaction with thiophenols on a large technical scale causes same problems due to the disagreeable odour of the mercaptans used.

Attempts have already been made in practice to introduce diffusion-fast hydrophobic couplers into the layer by introducing solubilizing groups in an alkaline solution. The groups used are generally carboxyl groups or sulfa groups. However, the disadvantage of these couplers is that they usually recrystallize from the emulsion as soon as the alkaline solutions are neutralized so that they are very difficult to introduce into the silver halide emulsion in a finely divided emulsified form. In cyan couplers of the naphthol series described in U.S. Pat. No. 3,556,796, solubility of the couplers in alkalis and ease of emulsification are ensured by certain sulfonamide groups arranged in a particular way in the coupler molecule.

Analogous yellow couplers, e.g. those according to British Pat. Nos. 1,187,860 and 1,159,357, are however by no means soluble in alkalis and it is therefore required in practice to prepare yellow couplers which can be easily obtained and easily emulsified and which do not have the disadvantages mentioned above.

The yellow couplers used are generally compounds having an active methylene group which can usually be derived from open-chain ketone methylene compounds such as -ketocarboxylic acid derivatives, in particular pivaloyl acetanilides or benzoyl acetanilides.

It has been found that diffusion-fast yellow couplers which have excellent emulsifiability are obtained by introducing a substituted or unsubstituted 2-cyclotetramethylene sulfone group into a non coupling position of yellow colorcoupler molecules preferably into the anilide portion of -ketoacetanilides.

The preferred embodiment of the invention therefore relates to a light-sensitive photographic material having at least one silver halide emulsion layer, characterized by containing a diffusion-fast color coupler of the following formula:

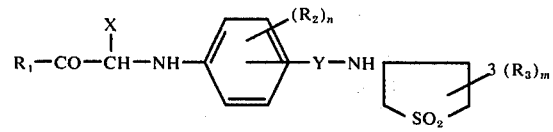

wherein:

Y is —CO—, —SO$_2$— or —NH—CO—;

X is H or a group which can be split off;

R$_2$ is H, halogen, cyanogen, alkoxy, aroxy, alkyl thio, aryl thio, dialkylamino or alkyl, in particular CH$_3$, the groups R$_2$ being either identical or different;

n is 1 to 4, preferably 1 or 2;

R$_3$ is H or alkyl with 1 – 4 C-atoms, preferably methyl;

m is 0, 1 or 2;

R$_1$ is (1) an alkyl group with 1 – 32 C-atoms, preferably 1 –18 C-atoms, which may be straight chained or branched, the secondary or tertiary carbon atom in the case of a secondary or tertiary alkyl group preferably being directly attached to the carbonyl group, more preferably a t-butyl group; (2) an alkoxy alkyl group; (3) a dicycloalkyl group; (4) a heterocyclic group or (5) an aryl group, in particular a phenyl group, optionally substituted one or more times with an alkyl group containing 1 – 18 C-atoms, preferably an ortho alkoxy group, aroxy, aryl, halogen (e.g. fluorine, chlorine or bromine), acyl, acyloxy, acylamino, amino, carbamyl, sulfamyl, sulfonyl or carboxy.

The yellow couplers according to the invention are therefore 2- equivalent or 4-equivalent yellow couplers and in the case of 2-equivalent yellow couplers the group X which can be split off by chromogenic development denotes, for example, halogen such as chlorine or fluorine, sulfo, SCN, acyloxy such as sulfonyloxy, alkoyloxy or aroyloxy, in particular benzoyloxy cyclooxy, aryloxy such as naphthoxy or phenoxy, heterocycloxy such as pyridinyloxy, tetrahydropyranyloxy or tetrahydropyranyloxy or tetrahydroquinolyloxy, an alkyl, aryl or heterocyclic azo group, an alkyl, aryl or heterocyclic mercapto group, a cyclic acid imide such as phtalimides, 2-pyridones and 2 pyridazones which are described in German Offenlegungsschriften DT-OS Nos. 2,213,461, 2,057,541, and 2,318,807, British Pat. No. 1,331,179, a benzotriazolyl group or a heterocyclic 5-membered nitrogen-containing groups ,having a —C=C— double bond adjoining to the nitrogen atom which in term is attached to the coupling position of the coupler molecule, which heterocyclic groups are disclosed in British patent application Ser. No. 25331/74.

The preferred yellow couplers according to the invention are those of the above formula in which $R_1$ is an alkyl group, preferably a t-butyl group, or a phenyl group as defined above. In cases where $R_1$ is a phenyl group, it may be substituted one or more times, preferably 1 to 3-times optionally with alkoxy groups, and the above mentioned acyl, acyloxy and acylamino groups may be derived from aliphatic, araliphatic or aromatic sulfonic or carboxylic acids, and one or both hydrogen atoms of the above mentioned amino, carbamyl, sulfamyl or sulfonyl groups may be replaced by indentical or different aliphatic, araliphatic, aromatic or heterocyclic groups.

The new color couplers prove to be very useful because they are highly soluble both in aqueous alkaline solutions, optionally with the addition of lower alcohols, and in organic solvents which are immiscible with water, such as ethyl acetate or methylene chloride, and also they can be dispersed in an extremely finely divided form at high concentrations. Their tendency to crystallize from dispersions and emulsions is distinctly reduced so that it is generally unnecessary to add oily coupler solvents. The high coupling activity of the couplers can therefore be fully utilized since the couplers are not enclosed in hydrophobic oil droplets.

The yellow couplers according to the invention may also be advantageously dispersed by the additional use of oily coupler solvents such as dibutyl phthalate or tricresyl phosphate, and it is unexpectedly found that in this case their coupling reactivity is in no way reduced.

It is unexpectedly found that the coupling reactivity of the yellow couplers according to the invention, in particular the yellow couplers of the above formula in which Y is $SO_2$, is comparable with that of couplers of the known art which contain solubilizing groups and can therefore be introduced into the layer in alkaline solutions, as will be shown below.

The yellow couplers according to the invention used in light-sensitive photographic silver halide materials and developed chromogenically are also distinguished by having good resistance to heat and tropical conditions both before and after chromogenic development. The light-fastness of the dyes obtained is in no way reduced compared with that of corresponding dyes which do not contain a 2-cyclotetramethylene sulfone group.

Furthermore, when the color couplers according to the invention (which contain a 2-cyclotetramethylene sulfone group in the anilide portion) are compared with corresponding color couplers which contain open-chain sulfonamido groups in the anilide portion instead of the 2-cyclotetramethylene sulfone group, e.g. the color couplers described in British Pat. Nos. 1,187,860 and 1,159,357, it is surprisingly found that although both types of coupler have basically the same high melting point, the color couplers according to the present invention are considerable more stable in dispersion than the couplers known in the art, which are generally found to crystallise from the emulsion when left to stand for only a short time and are difficult to introduce into the emulsion and even then can only be introduced at low concentrations so that they are very difficult to use in practice.

The following are examples of suitable couplers which are used according to the invention:

Dye No.
1

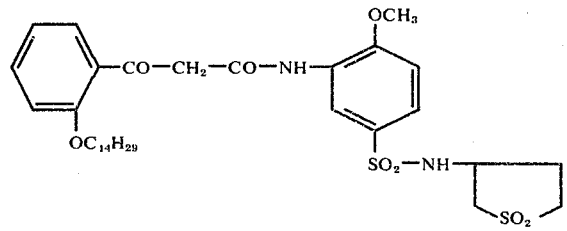

Mp. 124–125° C

2

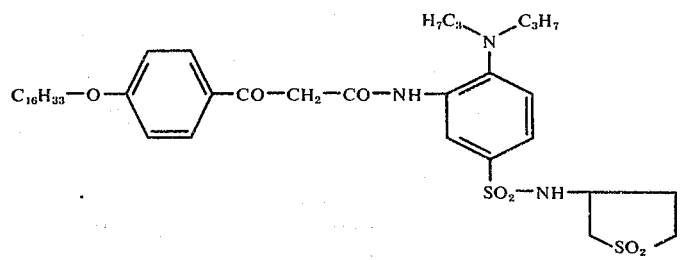

Mp. 77–78° C

| Dye No. | |
|---|---|
| 3 | 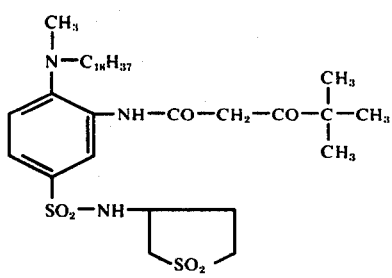 Mp. 91–94° C |
| 4 | 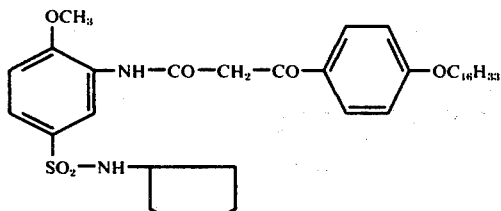 Mp. 126–135° C |
| 5 | 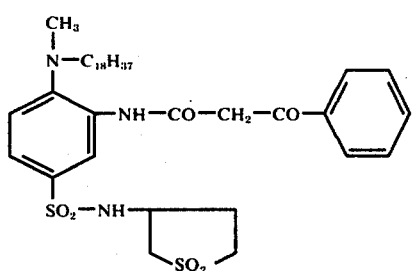 Mp. 102–104° C |
| 6 | 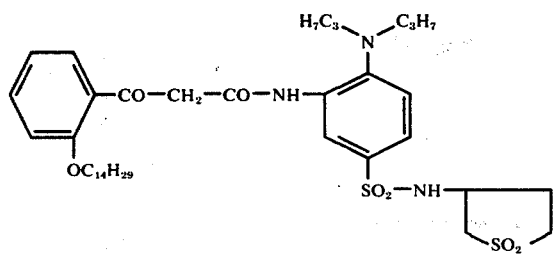 Mp. 76–78° C |
| 7 | 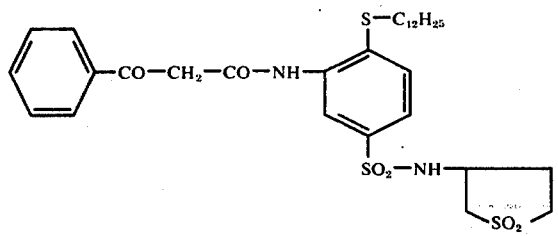 Mp. 144–145° C |
| 8 | 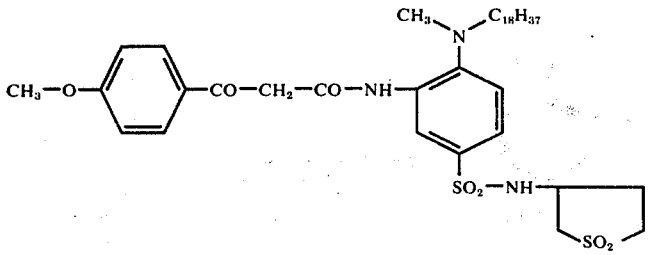 Mp. 102–104° C |

| Dye No. | |
|---|---|
| 9 | 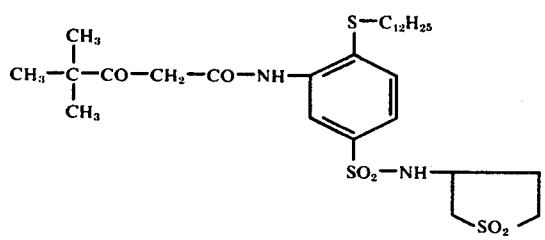<br>Mp. 142–143° C |
| 10 | 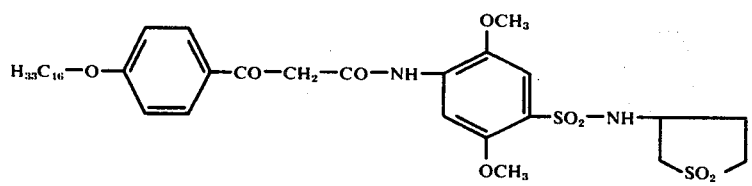<br>Mp. 159–160° C |
| 11 | 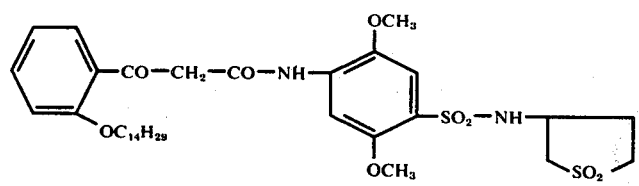<br>Mp. 124–125° C |
| 12 | 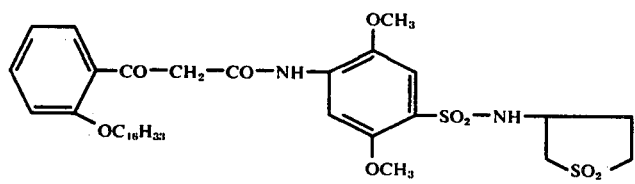<br>Mp. 120–121° C |
| 13 | 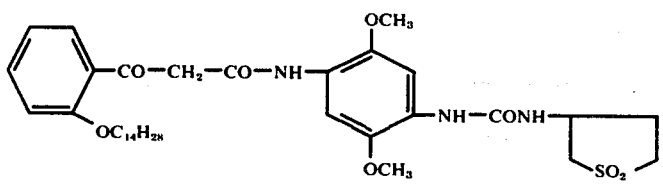<br>Mp. 137–138° C |
| 14 | 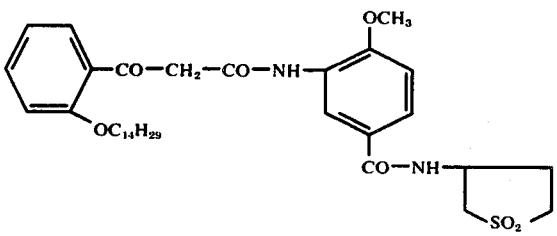<br>Mp. 74–75° C |
| 15 | 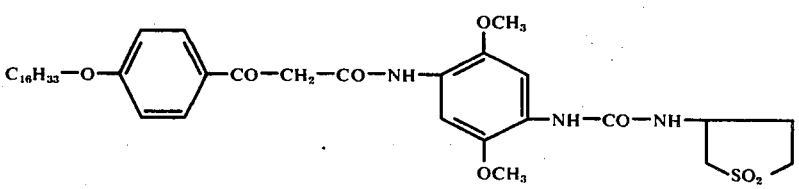<br>Mp. 150° C |

-continued
Dye No.
16
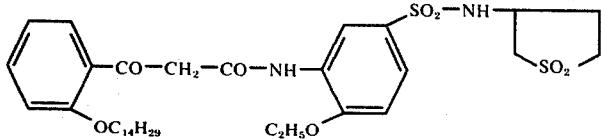
Mp. 101–102° C
17
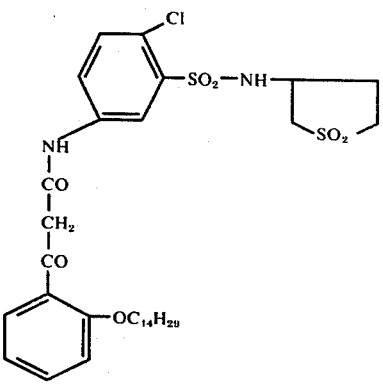
Mp. 109–110° C
18
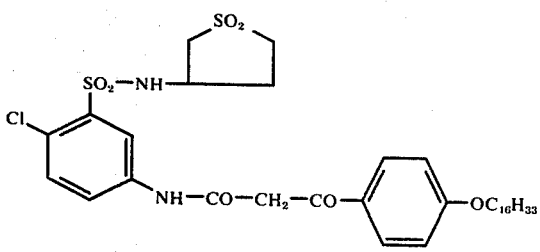
Mp. 161–162° C
19
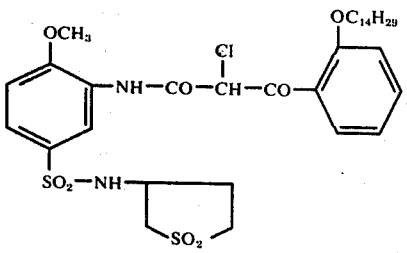
Mp. 109–110° C
20
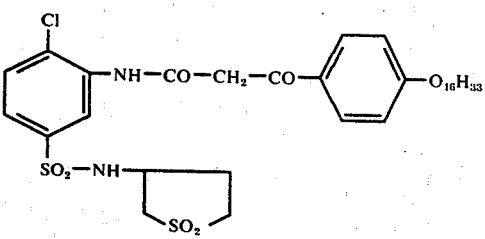
Mp. 155–157° C
21
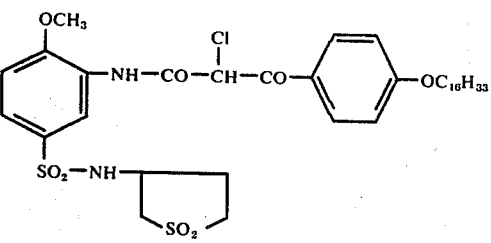
Mp. 122–123° C -continued
Dye No.
22
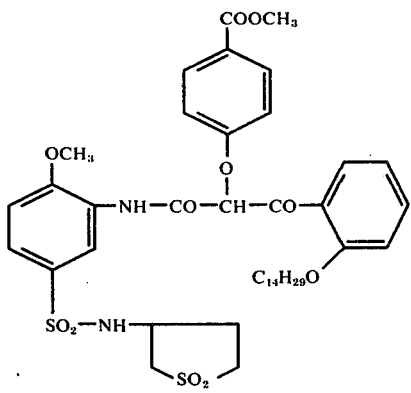
Mp. 133–134° C
23
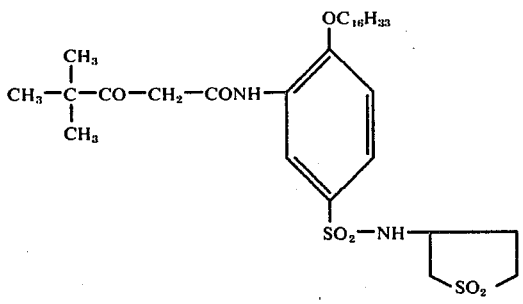
Mp. 128° C
24
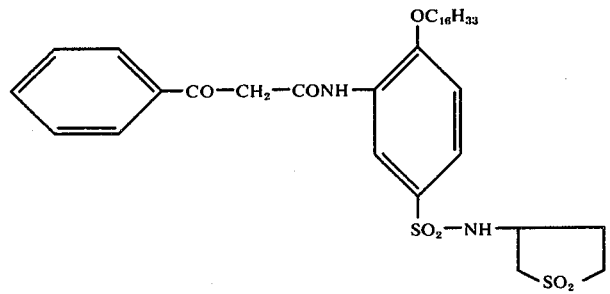
Mp. oily
25
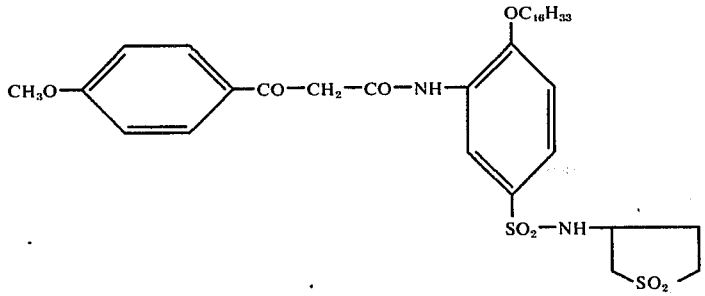
Mp. 132–135° C -continued
Dye No.
26
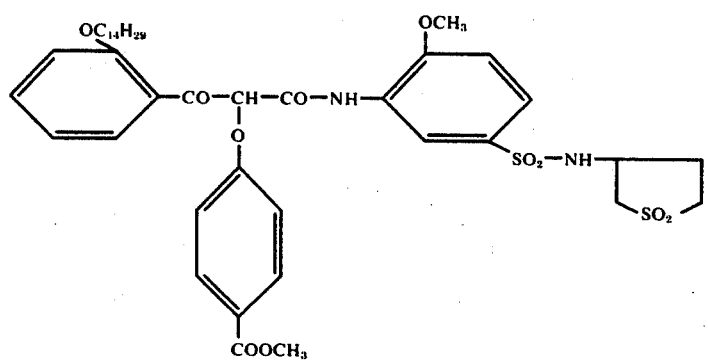
Mp. 132–135° C
27
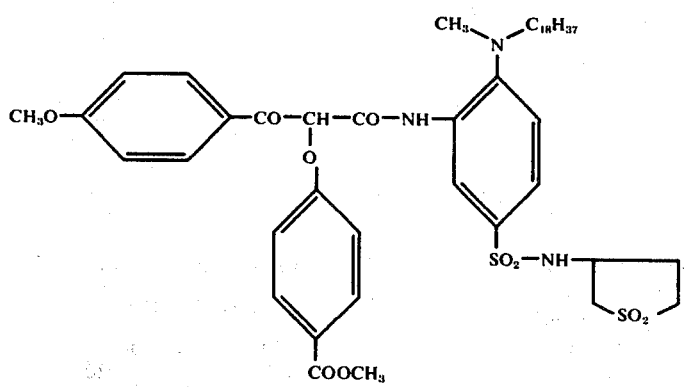
Mp. 115–116.5° C
28
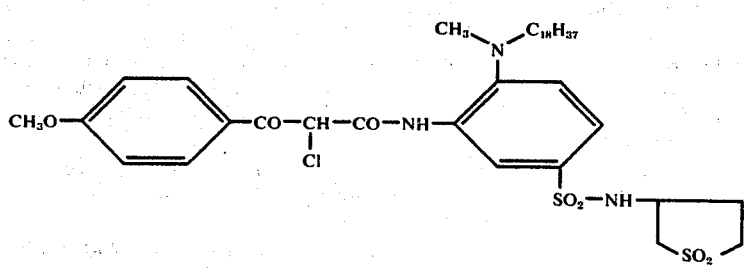
Mp. 92–93° C
29
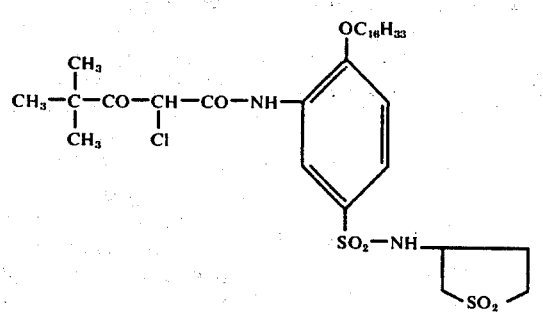
Mp. 113–114° C
30
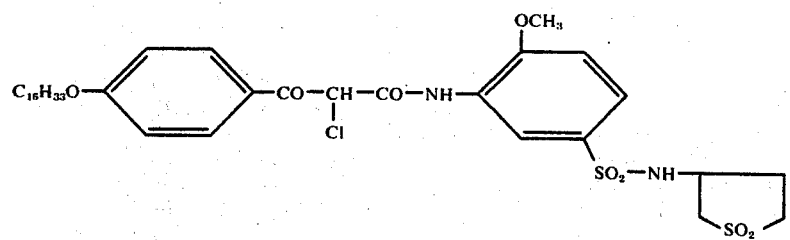
Mp. 122–123° C

| Dye No. | |
|---|---|
| 31 | 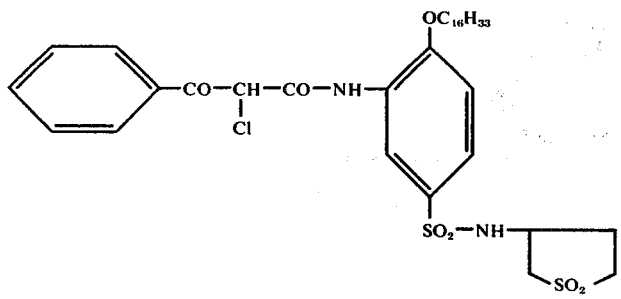 |
| | Mp. 88–90° C |
| 32 | 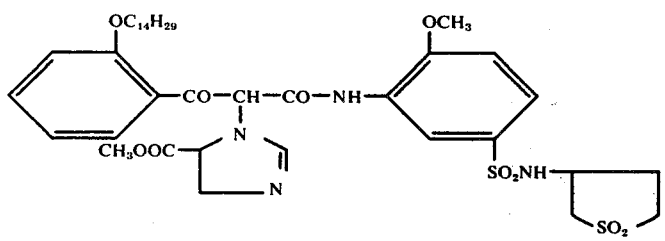 |
| | Mp. oily |

Preparation of the yellow couplers according to the invention is carried out by methods which are known per se. 2-amino-cyclotetramethylene sulfon is prepared from dihydrocyclotetramethylene sulfone or a corresponding substituted compound as described in German Pat. No. 682,079 and reacted with a suitably substituted nitrophenyl sulfonic acid chloride carboxylic acid or a aminocarboxylic acid in a suitable solvent, e.g. tetrahydrofuran, at room temperature. The resulting reaction product is hydrogenated to the corresponding amine compound, using Raney nickel as catalyst, and then converted to the coupler by reaction with acetoacetic esters in a suitable solvent such as dimethylformamide at elevated temperatures, e.g. 150° C.

The preparation of coupler 1 is described in detail below.

1ST STAGE 720 g (4 mol + 20%) of 2 amino-cycloletramethylene sulfone are suspended in 2000 ml of tetrahydrofuran, and 607.2 ml of triethylamine are then added. 1112 g (4 mol) of 2-nitroanisol-sulfonic acid chloride (96.1%) are then added in portions at 20° – 25° C. The reaction mixture is stirred for half an hour and then divided into two halves. Each half is vigorously stirred into 6000 ml of water. Both halves are then filtered through a suction filter and washed with $H_2O$ and methanol. The resulting product is again suspended in 6000 ml of water and dissolved in 5n NaOH. After purification with active charcoal and precipitation with 50% acetic acid (800 ml), the precipitate is suction-filtered and washed successively with water, methanol and diethyl ether. Yield 1202.5 g; Mp : 175°–177° C.

2ND STAGE 1202.5 g of the reaction product from stage 1 are dissolved in 1600 ml of dimethylformamide and catalytically hydrogenated in known manner, using Raney nickel as catalyst. The reaction product is then freed from catalyst in known manner, the solvent is removed and the oily residue is recrystallized from methanol.

Total yield: 1006.5 g, M.p.: 171°–172° C.

3RD STAGE 160 g (0.5 mol) of the reaction product from stage 2 and 222.2 g (0.5 mol + 10%) of o-tetradecyloxy-benzoyl acetic ester and 50 ml of dimethylformamide are heated on an oil bath at a temperature of 150° C for 3 hours. Dimethylformamide is then distilled off in a water jet vacuum at 170° C. The hot melt is stirred into ethanol and coupler 1 which separates when the mixture is left to stand overnight, is suction-filtered and washed with ethanol and ether. The coupler compound is purified by recrystallization from ethanol and washing the filtrate with ethanol and ether. Yield: 184 g, Mp.: 125° –126° C.

The compounds according to the invention are valuable diffusion-fast color couplers which, when chromogenically developed, yield dyes with excellent dispersion properties. They are eminently suitable for use in light-sensitive silver halide emulsion layers of color photographic single-layered or multi-layered materials. The color couplers need not necessarily be incorporated in the light-sensitive layers but may be incorporated in a layer of binder adjacent to a light-sensitive silver halide emulsions layer.

The yellow couplers according to the invention may be incorporated in the silver halide emulsion or some other binder mixture by a known method. Since the couplers according to the invention are so-called emulsification couplers, i.e. hydrophobic compounds, their incorporation in the photographic layer is carried out in known manner by dissolving them in suitable organic solvents, e.g. in esters of aliphatic carboxylic acids, particularly in acetic esters, or in methylene chloride and then emulsifying this solution in the silver halide emulsion which is ready for casting.

As already mentioned above, the yellow couplers according to the invention may also be introduced into the layer in a dispersed form with the aid of high-boiling oily coupler solvents. Examples of suitable oil-forming agents which may be used according to the invention include e.g. high-boiling acids such as dibenzyl acetic acid or phenyl ethyl acetic acid or their esters, in particular phthalic acid esters, of which dialkyl phthalic acid ester is particularly suitable, in particular dibutyl phthalate, high-boiling ketones such as benzophenone or methyl-isobutyl ketones or phosphoric acid esters such as triaryl phosphoric acid esters, e.g. tricresyl phosphate.

According to a preferred embodiment of the invention, incorporation of the yellow couplers in the emulsion is carried out by dissolving the couplers, preferably in low-boiling solvents such as ethyl acetate, methylene chloride or alkylene chloride, with the addition of a high-boiling solvent such as dibutyl phthalate.

According to another preferred embodiment of the invention, incorporation of the yellow couplers into the emulsion is carried out by dissolving the couplers in an aqueous alkaline solution, optionally with the addition of alcohol such as methanol or ethanol, and incorporating this solution into the silver halide emulsion which is ready for casting. As already mentioned above, compounds of the above formula in which Y is —$SO_2$— are particularly suitable for this embodiment of the process.

The light-sensitive emulsions used may be emulsions of silver halides such as silver chloride, silver bromide or mixtures thereof, optionally having a small silver iodide content of up to 10 mol %, in one of the usual hydrophilic binders. The binder used for the photographic layer is preferably gelatine although this may be partly or completely replaced by other natural or synthetic binders. Suitable natural binders are e.g. alginic acid and its derivatives such as salts, esters or amides, cellulose derivatives such as carboxymethyl cellylose, alkyl celluloses such as hydroxyethyl cellulose, starch or derivatives thereof such as ethers or esters, or carraghenates. Suitable synthetic binders are e.g. polyvinyl alcohol, partly saponified polyvinyl acetate or polyvinylpyrrolidone.

The emulsions may also be chemically sensitized, e.g. by adding sulfur compounds when the emulsions are being chemically ripened, for example allyl isothiocyanate, allyl thiourea or sodium thiosulfate and the like. The chemical sensitizers used may also be reducing agents, e.g. the tin compounds described in Belgian Pat. Nos. 493,464 and 568,687, or polyamines such as diethylene triamine or aminomethane sulfinic acid derivatives, e.g. according to Belgian Pat. No. 547,323.

Noble metals such as gold, platinum, palladium, iridium, ruthenium or rhodium and their compounds are also suitable chemical sensitizers. This method of chemical sensitization has been described in the article by R. KOSLOWSKY, Z. Wiss. Phot. 46, 65 – 72 (1951).

The emulsions may also be sensitized with polyalkylene oxides derivatives, e.g. with a polyethyline oxide having a molecular weight between 1000 and 20,000, or with condensation products of alkylene oxides and aliphatic alcohols, glycols, cyclic dehydration products of hexitols, alkyl-substituted phenols, aliphatic carboxylic acids, aliphatic amines, aliphatic diamines and amides. The condensation products have a molecular weight of at least 700, preferably more than 1000. These sensitisers, may, of course, be combined for the purpose of obtaining special effects, as described in Belgian Pat. No. 537,278 and in British Pat. Specification No. 727,982.

The emulsions must have a sufficient sensitivity in the blue region of the spectrum. Unsensitized emulsions in which the sensitivity is due to the intrinsic sensitivity of the silver halides used are generally employed for this purpose although the silver halide emulsions may also be sensitized to the blue region of the spectrum, e.g. by means of sensitizers of the kind described in German Pat. No. . . . . (P 18 08 041.6).

The emulsions may contain usual stabilizers e.g. homopolar or salt-type compounds of mercury which contain aromatic or heterocyclic rings, such as mercaptotriazoles, simple mercury salts, sulfonium mercury double salts and other mercury compounds. Azaindenes are also suitable stabilizers, especially tetra- or pentaazaindenes and particularly those which are substituted with hydroxyl or amino groups. Compounds of this kind have been described in the article by BIRR, Z. Wiss. Phot. 47, 2 – 58 (1952). Heterocyclic mercapto compounds such as phenyl mercaptotetrazole, quaternary benzothiazole derivatives or benzotriazole and the like are also suitable stabilizers, among others.

The emulsions may be hardened in the usual manner, for example with formaldehyde or halogenated aldehydes which contain a carboxyl group such as mucobromic acid, diketones, methane sulfonic acid esters or dialdehydes and the like.

The usual color developers are used for producing the dyes, e.g. the usual aromatic compounds of the p-phenylene diamine series which contain at least one primary amino group. The following are examples of suitable colour developers: N,N-dimethyl-p-phenylene diamine, N,N-diethyl-p-phenylene diamine, monomethyl-p-phenylene diamine, 2-amino-5-diethyl-amino toluene, N-butyl-N-ω-sulfobutyl-p-phenylene diamine or 2-amino-5-(N-ethyl-N-β-methane sulfonamidoethylamino)-toluene and the like. Other suitable colour developers have been described, for example, in J. Amer. Chem. Soc. 73, 3000 – 3025 (1951).

EXAMPLE 1

20 mMol of the couplers indicated below are dissolved, in each case, in 30 ml of ethyl acetate with the addition of 10 g of dibutyl phthalate and emulsified in the usual manner in 200 ml of a 5% aqueous gelatine solution with the addition of 1.6 g of the sodium salt of dodecyl sulfonic acid.

The emulsion is then mixed with 850 g of a 7.5% gelatine solution which contains a dispersion of 19.3 g of silver bromide and the mixture is diluted with water until it has the required viscosity for casting.

Emulsion samples A, B and C contained compounds 1, 15 and 16, respectively, emulsion sample D contained compound 10 of British Pat. No. 1,187,860 and sample E contained compound 2 of British Pat. Spec. No. 1,159,357.

One part of each emulsion sample was immediately applied to a transparent layer support of cellulose triacetate.

Another part was left to stand for 3 weeks before it was cast.

For comparison, another emulsion is prepared in which 20 mMol of an alkali-soluble, readily emulsifiable standard coupler of the formula shown below was incorporated in the form of an aqueous alkaline solution into 200 ml of a 5% aqueous gelatine solution and after neutralization was mixed with 850 g of a 7.5% gelatine solution as described above and diluted to the required casting viscosity with water.

Comparison emulsion E contained the coupler of the following formula:

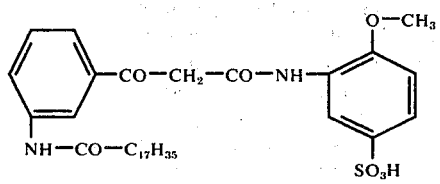

The materials prepared in this way are exposed behind a grey step wedge and cut up into several samples. The various samples are developed in the usual color developers for 5 minutes, bleached and fixed. The following developer substances were used:

$E_1$ N,N-diethyl-p-phenylene diamine $E_2$ 4-amino-3-methyl-N-ethyl-N-methane sulfonamido ethyl aniline $E_3$ N,N-diethyl-3-methyl-p-phenylene diamine $E_4$ N-butyl-N-Δ-sulfobutyl-p-phenylene diamine.

Emulsions D – E which contained the couplers of the known art were not stable in storage and therefore became cloudy after a short time due to the crystallization of coupler compounds.

The photographic materials obtained by immediately casting emulsion D – E were also unstable in storage. If freshly prepared photographic materials containing couplers D – E are immediately exposed and processed, no sufficient color density (density less than 1) could be obtained in materials prepared in this way because the crystallization of the coupler takes place even during the chromogenic development of the material.

Table 1 shows the sensitometric assessments of samples A – C according to the invention and of comparison sample F, which were prepared immediately after emulsification:

introduced in alkaline solution. In particular, it is advantageous that the maximum densities obtained with the couplers according to the invention are substantially as equally as high as those obtained with the alkali soluble standard coupler.

EXAMPLE 2

Sample A 20 mMol of coupler No. 5 are dissolved in 30 ml of ethyl acetate with the addition of 10 g dibutyl phthalate and emulsified in the usual manner in 200 ml of a 50% aqueous gelatine solution with the addition of 1.6 g of the sodium salt of dodecyl sulfonic acid and then treated as described in example 1. After the emulsion has been cast on a transparent layer support of cellulose triacetate, the photographic material prepared in this way is exposed behind a grey step wedge and cut into several samples.

3sample strips are immediately developed for 5 minutes in a color developer containing $E_1$ as the developer substance and bleached and fixed as described in example 1.

Another strip is subjected to a heat test before the photographic process (7 days' storage at 57° C and 34% atmospheric moisture).

A further strip is subjected to a tropical test before the photographic process (7 days' storage at 35° C and 85% atmospheric humidity).

Yellow step wedges with an absorption maximum of 436 Nm are obtained.

A strip of the samples which were untreated before development is then exposed to a tropical test (7 days' storage at 60° C and 100% atmospheric humidity) and another strip is exposed to a heat test (7 days' storage at 77° C and 5% atmospheric humidity).

Emulsion B is prepared and processed in analogous manner with the exception that instead of 20 mMol of Table 1

| Coupler | Developer | Sensitivity | Fog yellow | Fog magenta | Fog cyan | Density | Absorption (%) yellow | Absorption (%) magenta | Absorption (%) cyan |
|---|---|---|---|---|---|---|---|---|---|
| 1 | $E_1$ | 9.2 | 8 | 8 | 8 | 2.1 | 100 | 3 | 0 |
|  | $E_2$ | 9.8 | 10 | 8 | 8 | 1.8 | 100 | 4 | 2 |
|  | $E_3$ | 10.2 | 12 | 9 | 9 | 2.1 | 100 | 3 | 1 |
|  | $E_4$ | 7.4 | 11 | 8 | 8 | 2.5 | 100 | 6 | 2 |
| 15 | $E_1$ | 9.8 | 8 | 7 | 8 | 2.3 | 100 | 3 | 1 |
|  | $E_2$ | 11.5 | 9 | 9 | 9 | 1.9 | 100 | 3 | 0 |
|  | $E_3$ | 10.9 | 8 | 8 | 8 | 1.8 | 100 | 4 | 1 |
|  | $E_4$ | 9.7 | 8 | 8 | 8 | 2.3 | 100 | 4 | 1 |
| 16 | $E_1$ | 9.6 | 9 | 8 | 7 | 2.1 | 100 | 3 | 1 |
|  | $E_2$ | 11.2 | 8 | 8 | 8 | 1.6 | 100 | 5 | 0 |
|  | $E_3$ | 10.0 | 8 | 7 | 8 | 1.7 | 100 | 5 | 1 |
|  | $E_4$ | 9.7 | 8 | 8 | 8 | 2.1 | 100 | 5 | 1 |
| Comparison coupler | $E_1$ | 8.6 | 9 | 9 | 9 | 2.4 | 100 | 6 | 1 |
|  | $E_2$ | 8.8 | 12 | 8 | 8 | 2.2 | 100 | 9 | 2 |
|  | $E_3$ | 8.2 | 15 | 9 | 9 | 2.2 | 100 | 8 | 1 |
|  | $E_4$ | 6.9 | 17 | 9 | 9 | 2.6 | 100 | 7 | 1 |

Sensitometric assessment of samples A – C according to the invention which were stored for 3 weeks before casting showed that no change in the values in the above table occurred. The couplers according to the invention therefore have excellent stability in storage.

As indicated by the sensitometric assessment in the above table 1, the couplers according to the invention are also distinguished by their high reactivity, high sensitivity, low fog values and low side absorptions. It is unexpectedly found that the photographic properties of the yellow couplers according to the invention which were incorporated into the layers in emulsified form are comparable with those of the standard coupler coupler No. 5 dissolved in ethyl acetate, 20 mMol of coupler No. 4 dissolved in ethylene chloride are introduced.

Another emulsion sample C is prepared into which 20 mMol of coupler No. 3 dissolved in ethyl acetate are introduced without the addition of dibutyl phthalate.

The sensitometric assessments are shown in the following table 2. To assess the stability under tropical conditions and heat, the reduction of the maximum density or of density 0.5 or 1.5 is indicated in percent compared with the corresponding density of untreated samples. For comparison, the table also shows the sensitometric assessment of a comparison material containing the alkali soluble comparison coupler as in example 1.

comparable to or even higher than that of the alkali soluble standard coupler.

Analogous results are obtained when couplers 5, 4 and 3 are dissolved not in the solubilizing agent indicated above but in 20 ml of ethyl acetate, 10 ml of tricresyl phosphate, 20 ml of ethylene chloride, 10 g of dibutyl phthalate or 20 ml of a 10% aqueous sodium hydroxide solution and 10 ml of an alcohol such as methanol or ethanol and then incorporated in the emulsion in the usual manner.

Table 2

|  | Coupler 5 | Coupler 4 | Coupler 3 | Comparison coupler |
|---|---|---|---|---|
| Absorption maximum | 442 | 441 | 436 | 445 |
| Density | 2.8 | 2.9 | 2.1 | 2.1 |
| Reduction of maximum density in % in the tropical test before development | 0 | −17 | −8 | −10 |
| Reduction of maximum density in % in the heat test before development | −8 | 0 | 0 | 0 |
| Reduction of density in % in the tropical test after development at | | | | |
| 0.5 | 15 | 0 | 0 | 50 |
| density 1.5 | 9 | 6 | 0 | 64 |
| of density in % in heat test after development at | | | | |
| 0.5 | 0 | 0 | 0 | 0 |
| density 1.5 | 0 | 0 | 0 | 0 |

As can be seen from table 2, the yellow couplers according to the invention have a high stability to storage under moist, warm conditions and particularly their stability to storage in heat, both before and after chromogenic development. The density of the yellow couplers according to the invention is, like in example 1,

EXAMPLE 3

1. an emulsion containing 20 mMol of coupler No. 8 is prepared as described in example 1 processed as described in examples 1 and 2. Various samples are subjected to a tropical test or heating cupboard test as described in example 2. The following table 3 shows the sensitometric assessments of the yellow step wedges.

Table 3

| Developer | Absorption maximum (nm) | Sensitivity | Maximum density | Tropical test Reduction of density in % for at maximum density | Tropical test Reduction of density in % after development at density 0.5 | Tropical test Reduction of density in % after development at density 1.5 | Heat test Reduction of density in % before at maximum density | Heat test Reduction of density in % after development at density 0.5 | Heat test Reduction of density in % after development at density 1.5 | Absorption (%) yellow | Absorption (%) magenta | Absorption (%) cyan |
|---|---|---|---|---|---|---|---|---|---|---|---|---|
| $E_1$ | 441 | 9.0 | 2.5 | −5 % | 10 | 7 | 0 | 0 | 0 | 100 | 4 | 1 |
| $E_2$ | 450 | 9.4 | 1.8 | — | 0 | 0 | — | 0 | 0 | 100 | 4 | 0 |
| $E_3$ | 450 | 8.4 | 1.8 | — | 10 | 4 | — | 0 | 0 | 100 | 4 | 1 |
| $E_4$ | 448 | 8.7 | 2.2 | — | 0 | 21 | — | −10 | 8 | 100 | 4 | 1 |

2. A photographic material was prepared, exposed and processed as described in 1.) except that coupler No. 7 dissolved in 20 ml of ethylene chloride and 10 g of dibutyl phthalate was introduced into the emulsion instead of coupler No. 8. The sensitometric assessments of the step wedges obtained in this way are shown in the following table 4.

Table 4

| Developer | Absorption maximum (nm) | Sensitivity | Maximum density | Tropical test Reduction of density in % before development at maximum density | Tropical test Reduction of density in % after development at density 0.5 | Tropical test Reduction of density in % after development at density 1.5 | Heat test Reduction of density in % before development at maximum density | Heat test Reduction of density in % after development at density 0.5 | Heat test Reduction of density in % after development at density 1.5 | Absorption (%) yellow | Absorption (%) magenta | Absorption (%) cyan |
|---|---|---|---|---|---|---|---|---|---|---|---|---|
| $E_1$ | 450 | 8.5 | 3.0 | −26 | −14 | −10 | 0 | 0 | 0 | 100 | 11 | 7 |
| $E_2$ | 458 | 8.8 | 1.8 | — | 0 | 0 | — | 0 | 0 | 100 | 10 | 2 |
| $E_3$ | 462 | 8.1 | 2.3 | — | 0 | 0 | — | 0 | 0 | 100 | 9 | 2 |
| $E_4$ | 454 | 8.0 | 2.6 | — | −42 | −42 | — | 0 | 0 | 100 | 4 | 0 |

3. A photographic material was prepared, exposed and processed as described under 2.) except that coupler No. 8 was used instead of coupler No. 7. The sensitometric assessments of the step wedges obtained in this way are shown in the following table 5.

Table 5

| developer | Absorption maximum (nm) | Sensitivity | Maximum density | Tropical test reduction of density in % before development at maximum density | Tropical test reduction of density in % after development at density 0.5 | Tropical test reduction of density in % after development at density 1.5 | Heat test reduction of density in % before development at maximum density | Heat test reduction of density in % after development at density 0.5 | Heat test reduction of density in % after development at density 1.5 | Absorption(%) yellow | Absorption(%) magenta | Absorption(%) cyan |
|---|---|---|---|---|---|---|---|---|---|---|---|---|
| $E_1$ | 442 | 9.4 | 2.2 | −9 | −8 | −7 | 0 | 0 | 0 | 100 | 2 | 1 |
| $E_2$ | 452 | 9.5 | 1.8 | — | 0 | 0 | — | 0 | 0 | 100 | 3 | 0 |
| $E_3$ | 456 | 8.5 | 1.7 | — | −8 | −4 | — | 0 | 0 | 100 | 3 | 0 |

Table 5-continued

| developer | Absorption maximum (nm) | Sensitivity | Maximum density | Tropical test reduction of density in % before development at maximum density | Tropical test reduction of density in % after development at density 0.5 | Tropical test reduction of density in % after development at density 1.5 | Heat test reduction of density in % before development at maximum density | Heat test reduction of density in % after development at density 0.5 | Heat test reduction of density in % after development at density 1.5 | Absorption(%) yellow | Absorption(%) magenta | cyan |
|---|---|---|---|---|---|---|---|---|---|---|---|---|
| $E_4$ | 447 | 8.4 | 1.8 | — | −22 | −35 | — | 0 | −6 | 100 | 3 | 1 |

As can be seen from tables 3–5, the yellow couplers according to the invention, in addition to their relatively high absorption maximum, are also distinguished by their high sensitivity, good maximum density, low side absorptions and low fog values. The stability under tropical conditions and heat is excellent both in the couplers according to the invention and in the dyes produced from them, particularly when $E_1$, $E_2$ and $E_3$ are used as a developer substance.

We claim:

1. A light-sensitive photographic material having at least one silver halide emulsion layer and a diffusion-fast 2- or 4-equivalent yellow coupler with an active methylene group which may be substituted by a group capable of being split off during color development wherein the improvement comprises the coupler is a B-ketoacetanilide containing the 2-cyclotetramethylene sulfone group in the anilide portion of the following formula:

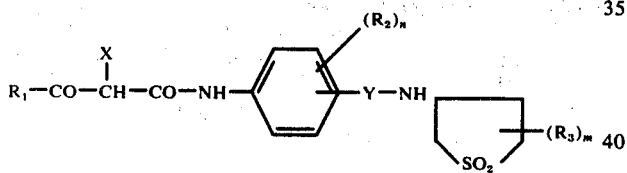

wherein:
Y is —CO—, —SO$_2$— or —NH—CO;
X is hydrogen or a group which can be split off;
$n$ is an integer from 1 to 4;
$R_2$ H, halogen, cyanogen, alkoxy, aroxy, alkylthio, arylthio, dialkylamino or alkyl, the groups represented by $R_2$ being identical or different;
$R_3$ is H or alkyl;
$m$ is 0, 1 or 2;
$R_1$ is alkyl of 1 to 32 C-atoms, alkoxy, alkyl, dicycloalkyl, a heterocyclic group or an aryl group which may be substituted with acyl, acyloxy, acylamino, amino, carboxyl, alkyl, alkoxy, aryl, aroxy, halogen or the groups selected of amino, carbamoyl, sulfamoyl or sulfonyl whereby one or both hydrogen atoms of the said groups may be replaced by identical or different aliphatic, araliphatic, or aromatic or heterocyclic groups.

2. A photographic material according to claim 1, in which $R_1$ is t-butyl group or phenyl group which may be substituted with acyl, acyloxy, acylamino, carboxyl, alkyl, alkoxy, aryl, aroxy, halogen or the groups selected of amino, carbamoyl, sulfamoyl or sulfonyl whereby one or both hydrogen atoms of the said groups may be replaced by identical or different aliphatic, araliphatic, or aromatic or heterocyclic groups.

3. A photographic material according to claim 1 in which $R_1$ is t-butyl group or phenyl group which may be substituted with from one to three times by acyl, acyloxy, acylamino, amino, carboxyl, alkyl, alkoxy, aryl, aroxy, halogen or groups selected of amino, sulfamyl, carbamyl or sulfonyl, whereby one or both hydrogen atoms of the said groups may be replaced by identical or different aliphatic, araliphatic, aromatic or heterocyclic groups, and Y is SO$_2$.

4. A photographic material according to claim 1, in which Y = — SO$_2$ —.

5. A photographic material according to claim 1, in which Y = —NH—CO—.